United States Patent [19]

Hayashi et al.

[11] Patent Number: 5,480,907

[45] Date of Patent: Jan. 2, 1996

[54] AROMATIC AMIDE COMPOUNDS AND THEIR PRODUCTION AND USE

[75] Inventors: Kyozo Hayashi; Munekazu Iinuma, both of Gifu, Japan

[73] Assignee: Takeda Chemical Industries, Ltd., Osaka, Japan

[21] Appl. No.: 882,025

[22] Filed: May 13, 1992

[30] Foreign Application Priority Data

May 16, 1991 [JP] Japan .................................. 3-111973

[51] Int. Cl.⁶ .................................. A61K 31/35
[52] U.S. Cl. ........................... 514/457; 549/289
[58] Field of Search .................. 549/289; 514/457

[56] References Cited

U.S. PATENT DOCUMENTS 3,255,231  6/1966  Green et al. ................... 260/463

FOREIGN PATENT DOCUMENTS

| 0124791 | 11/1984 | European Pat. Off. . |
| 0333522 | 9/1989 | European Pat. Off. . |
| 0399814 | 11/1990 | European Pat. Off. . |
| 2153798 | 5/1972 | Germany . |

OTHER PUBLICATIONS

King et al., Tetrahedron Letters, vol. 26, No. 11 1985 pp. 1415–1418.

Inoe et al., Chemical Abstracts, vol. 117, No. 5 (1992), p. 96 Abstract No. 40435m.

Schubert et al., Journal für Praktische Chemie, vol. 319, No. 5 (1977) pp. 745–754.

*Primary Examiner*—C. Warren Ivy
*Assistant Examiner*—A. A. Owens
*Attorney, Agent, or Firm*—Wenderoth, Lind & Ponack

[57] ABSTRACT

Aromatic amide compounds of the formula:

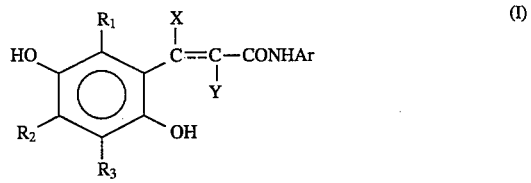

wherein $R_1$, $R_2$, and $R_3$ are independently hydrogen, a lower alkyl or lower alkoxy group; Ar is an optionally substituted aromatic group; the group

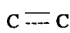

is C=C or HC—CH; X is hydrogen, $CH_2COOH$ or $CH_2CONHAr$; and Y is hydrogen or COOH; provided that when X is $CH_2COOH$ or Y is COOH, the COOH may be taken together with the adjacent hydroxy group on the benzene ring to form a lactone ring by dehydration, a quinone form thereof or a pharmaceutically acceptable salt thereof have potent nerve growth factor (NGF) secretion inducing activity, and are thus useful as a drug for the treatment or prophylaxis of degenerative nervous system disorders such as senilic dementis, and Alzheimer's disease.

10 Claims, 4 Drawing Sheets

AROMATIC AMIDE COMPOUNDS AND THEIR PRODUCTION AND USE

FIELD OF THE INVENTION

The invention relates to novel aromatic amide compounds exerting nerve growth factor (hereinafter referred to as NGF) secretion inducing activity, a composition comprising at least one of said compounds with a pharmaceutically acceptable carrier and a method for treating or preventing degenerative nervous system disorders associated with senilic dementis, Alzheimer's disease, etc.

The compounds of the present invention are of value as a medicine and particularly as a drug for the treatment or prevention of degenerative nervous system disorders including senilic dementis, Alzheimer's disease, etc.

BACKGROUND OF THE INVENTION

With the on-going uptrend in age distribution of the population, a variety of brain function improving agents have been proposed.

Nerve growth factor (NGF) has been considered to be a nutrient factor essential to the maintenance of the living body, which serves to promote differentiation of the sympathetic and sensory nerve cells and brain nerve cells in the stage of genesis. The characteristics of NGF as a chemical compound (protein) have also been elucidated [Nature, 302, 538, (1983)].

In patients bearing senile dementia or Alzheimer's disease, the biosynthesis and secretion of NGF are either at a low level or defected. Therefore, attempts have been made to use NGF for the treatment of maladies in degenerative nervous system disorders such as senile dementia and Alzheimer's disease [Nature, 329, 65, (1987)]. However, since the levels of biosynthesis and secretion of NGF are generally low, it is very difficult to isolate NGF from the living tissue or produce it by cloning in amounts useful for therapeutic and other purposes. On the other hand, it is known that NGF is synthesized in vivo in the sympathetic and sensory nerve cells and brain nerve cells [Biochemical Biophysical Research Communications, 136, 57, (1986)].

Under the circumstances, attempts have been made to stimulate the secretion of NGF in various nerve cells and cerebral neurons by means of catechol compounds [The Pharmaceuticals Monthly (Japan), 29, 49, (1987)]. However, these compounds are not satisfactory in the degree of activity or on the aspect of cytotoxicity.

From the above points of view, the inventors have made extensive research into developing an NGF secretion inducing agent that may take the place of cathecol compounds and have found that certain aromatic amide compounds have unexpectedly potent NGF secretion inducing activity.

SUMMARY OF THE INVENTION

The invention relates to novel aromatic amide compounds of the formula:

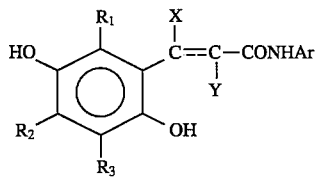
(I)

wherein $R_1$, $R_2$, and $R_3$ are independently hydrogen, a lower alkyl or lower alkoxy group; Ar is an optionally substituted aromatic group; the group $$C \text{---} C$$

is C=C or HC—CH; X is hydrogen, $CH_2COOH$ or $CH_2CONHAr$; and Y is hydrogen or COOH; provided that when X is $CH_2COOH$ or Y is COOH, the COOH may be taken together with the adjacent hydroxy group on the benzene ring to form a lactone ring by dehydration, a quinone form thereof or a pharmaceutically acceptable salt thereof.

The invention also relates to a NGF secretion inducing composition, which comprises an effective amount of at least one of the compounds of formula (I) or its quinone form or pharmaceutically acceptable salt, in admixture with a pharmaceutically acceptable carrier.

The invention further relates to a method for the prophylaxis or treatment of degenerative nervous system disorders which comprises administering to a mammal suffering from said disorders an effective amount of at least one of the compounds of formula (I) or its quinone form or pharmaceutically acceptable salt.

DETAILED DESCRIPTION OF THE INVENTION

Figure 1:
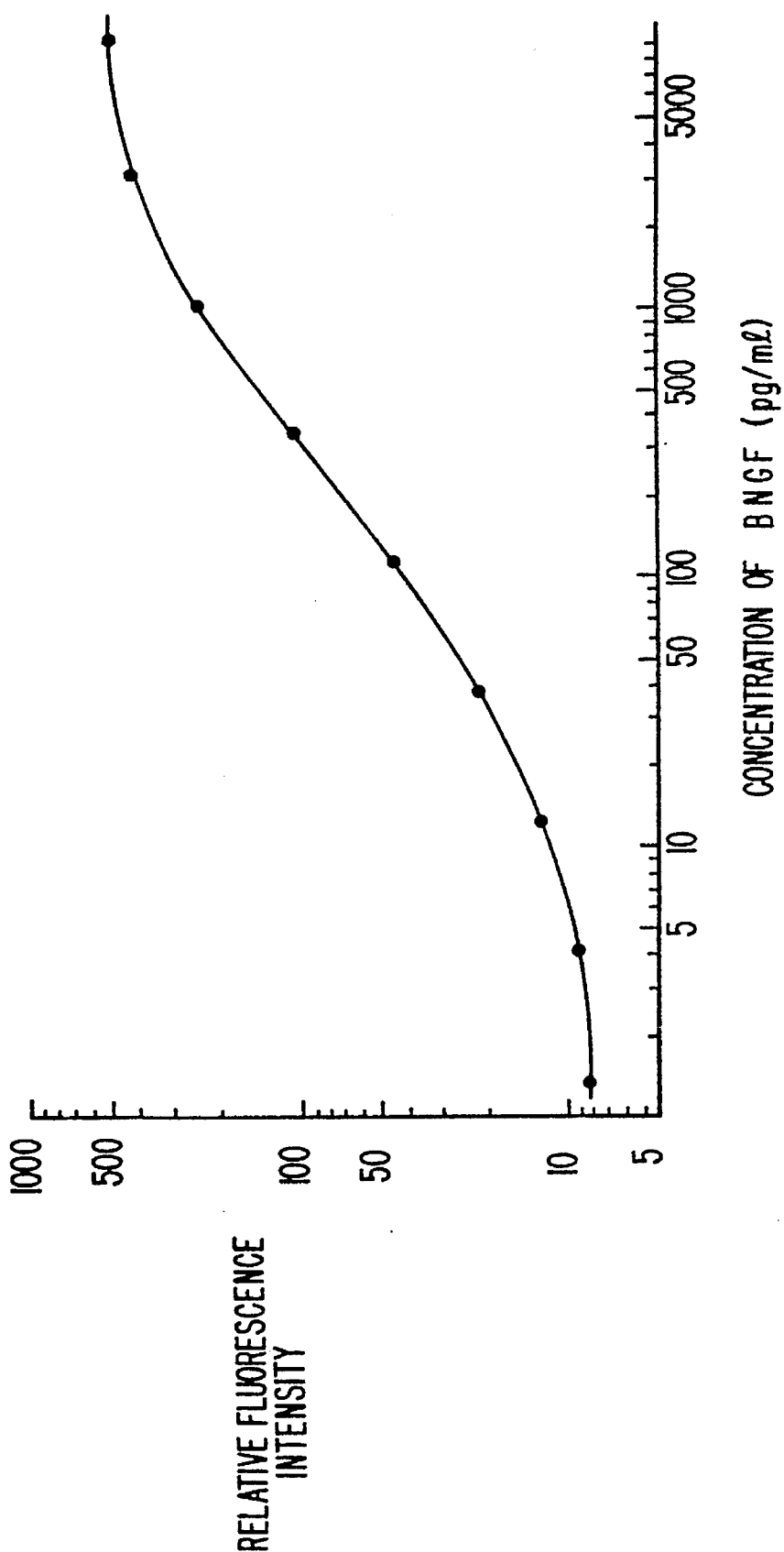
FIG. 1 shows the EIA standard curve of mouse β NGF according to the B-SA system method.

The present invention provides novel aromatic amide compounds having the formula:

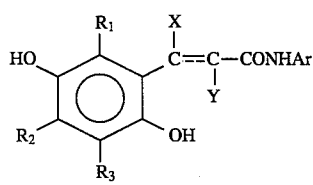
(I)

wherein $R_1$, $R_2$, and $R_3$ are independently hydrogen, a lower alkyl or lower alkoxy group; Ar is an optionally substituted aromatic group; the group $$C \text{---} C$$

is C=C or HC—CH; X is hydrogen, $CH_2COOH$ or $CH_2CONHAr$; and Y is hydrogen or COOH; provided that when X is $CH_2COOH$ or Y is COOH, the COOH may be taken together with the adjacent hydroxy group on the benzene ring to form a lactone ring by dehydration, a quinone form thereof or a pharmaceutically acceptable salt thereof.

In the foregoing formula (I), the lower alkyl for $R_1$, $R_2$, and $R_3$ is a straight or branched chain lower alkyl group of 1 to 15 carbon atoms such as methyl, ethyl, propyl, butyl, pentyl, hexyl, heptyl, octyl, decyl, dodecyl, pentadecyl and the like. The lower alkoxy for $R_1$, $R_2$, and $R_3$ is a straight or branched chain lower alkoxy group of 1 to 6 carbon atoms such as methoxy, ethoxy, propoxy, butoxy, hexyloxy, and the like. A preferred example for $R_1$ is hydrogen, straight chain lower alkyl of 1 to 10 carbon atoms such as methyl, ethyl, propyl, butyl, pentyl, hexyl, heptyl, decyl and the like or straight chain lower alkoxy group of 1 to 4 carbon atoms such as methoxy, ethoxy, n-propoxy, n-butoxy and the like. Among them, hydrogen or methyl is most preferable. A preferred example for $R_2$ and $R_3$ is hydrogen, straight chain lower alkyl of 1 to 6 carbon atoms such as methyl, ethyl, n-propyl, n-butyl, n-pentyl, n-hexyl and the like or straight chain lower alkoxy group of 1 to 3 carbon atoms such as methoxy, ethoxy, n-propoxy and the like. Among them, hydrogen or methyl is most preferable.

In the foregoing formula (I), the aromatic group Ar may be of 6 to 10 carbon atoms and includes phenyl, α-naphthyl, β-naphthyl, etc., which may be unsubstituted or substituted with one or more substituents. Examples of such substituents on the aromatic group for Ar include halogen (e.g. fluorine, chlorine, bromine, etc.), hydroxy, lower alkyl (e.g. lower alkyl of 1 to 4 carbon atoms such as methyl, ethyl, propyl, and the like), lower alkoxy (e.g. lower alkoxy of 1 to 3 carbon atoms such as methoxy, ethoxy and the like), nitro, etc.

In the foregoing formula (I), the group

is a double bond between carbon atoms (C=C) or a saturated chemical bond (CH—CH).

X is hydrogen, $CH_2COOH$ or $CH_2CONHAr$ wherein Ar is of the same meaning as defined above and Y is hydrogen or COOH.

When X is $CH_2COOH$ or Y is COOH, said COOH may be taken together with the adjacent hydroxy group on the benzene ring to form a lactone ring by dehydration.

In the case where X is $CH_2COOH$, the lactone form of the compound of formula (I) is represented by the following formula:

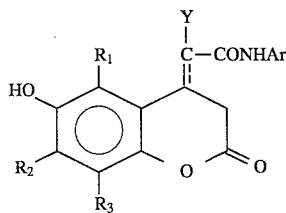

wherein $R_1$, $R_2$, $R_3$, Ar and Y have the same meanings as defined above.

In the case where Y is COOH, the lactone form of the compound of formula (I) is represented by the following formula:

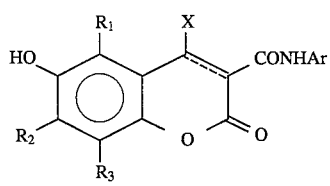

wherein $R_1$, $R_2$, $R_3$, Ar and X have the same meanings as defined above.

The quinone form of the compounds of formula (I) is represented by the following formula:

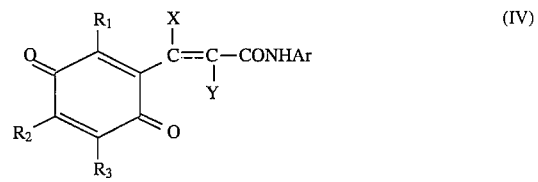

wherein $R_1$, $R_2$, $R_3$, Ar, X and Y have the same meanings as defined above.

In accordance with the present invention, a preferred embodiment includes a compound having the formula:

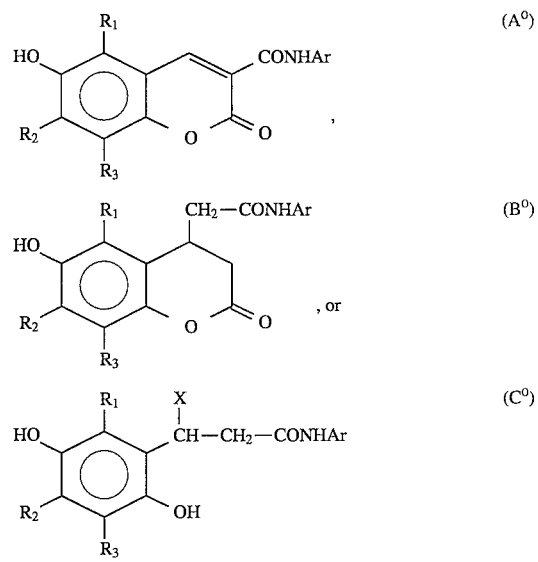

wherein X is hydrogen, $CH_2COOH$ or $CH_2CONHAr$ and $R_1$, $R_2$, $R_3$ and Ar have the same meanings as defined above.

Among the compounds represented by the above formula (I), a preferred example of the invention is a compound of the formula:

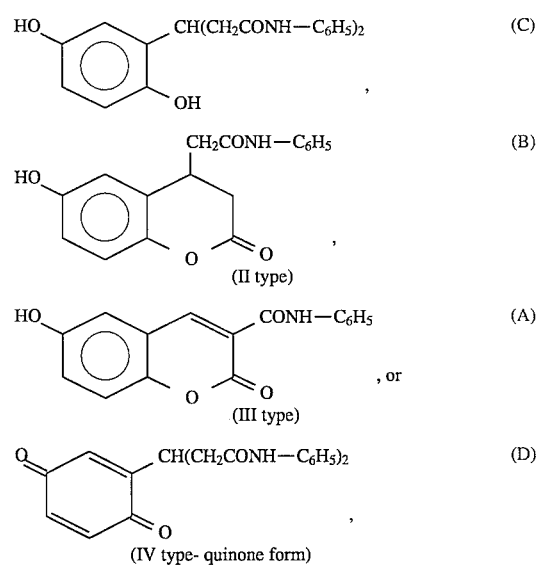

The compounds of formula (I) may form various salts according to the kinds of substituents thereon, such as salts with alkali metals (e.g. potassium, sodium, etc.) or alkaline earth metals (e.g. calcium, magnesium, etc.), and ammonium salts.

The compounds of formula (I) can be synthesized from 2,5-dihydroxybenzaldehyde derivatives (V), malonic acids (VI), and aniline derivatives (VII) in the presence of an organic base in a suitable solvent as illustrated below.

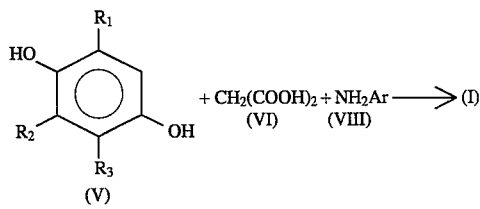

The solvents include conventional organic solvents, for example, aromatic hydrocarbon solvents such as benzene and toluene, ester solvents such as ethyl acetate and butyl acetate, ether solvents such as tetrahydrofuran and dibutyl ether, basic solvents such as pyridine and piperidine. The organic base includes butylamine, dibutylamine, cyclohexylamine, dicyclohexylamine, triethylamine, pyridine, piperidine, etc.

The base is used in a range of 0.001 to 0.1 molar amounts, preferably 0.005 to 0.05 molar amounts relative to 1 molar amount of the 2,5-dihydroxybenzaldehyde derivative (V). It is convenient to use a basic solvent such as pyridine and piperidine as the base as well as the solvent therefor. The reaction is carried out at temperature ranging from room temperature to 180° C., preferably from 50° to 130° C. The malonic acid (VI) is usually used in an excess amount (1.05 to 5 moles), preferably in a range of 1.5 to 2.5 molar amounts relative to 1 molar amount of the 2,5-dihydroxybenzaldehyde derivative (V). The aniline derivative (VII) is also used in an excess amount (2 to 20 moles) relative to 1 molar amount of the 2,5-dihydroxybenzaldehyde derivative (V). The reaction term usually ranges from 1 to 40 hours, preferably from 3 to 15 hours.

The 2,5-dihydroxybenzaldehyde derivative (V) and the aniline derivative (VII) may be commercially available or, in case where they are not commercially available, can be prepared by methods known in the art or analogous thereto.

The quinone form (IV) can be prepared by conventionally oxidizing the compound (I). The compounds (I) and (IV) can be isolated from the reaction solution by conventional processes such as extraction and purification.

The pharmaceutically active compounds of this invention may be used alone or formulated as pharmaceutical compositions comprising, in addition to the active ingredient, a pharmaceutically acceptable carrier or diluent. The compounds may be administered by a variety of means. Those of principal interest include: orally, topically or parenterally (intravenous or intramuscular injection). The pharmaceutical compositions may be in solid form such as capsules, tablets, powders, etc. or in liquid form such as solutions, suspensions or emulsions. Compositions for injection, the preferred route of delivery, may be prepared in unit dose form in ampules or in multidose containers and may contain formulatory agents such as suspending, stabilizing and dispersing agents. The compositions may be in ready to use form or in powder form for reconstitution at the time of delivery with a suitable vehicle such as sterile water.

For application as a nerve growth factor secretion inducing agent, the compounds of formula (I) can be formulated into various dosage forms, such as tablets, granules, capsules, injections, suppositories, etc., in the per se conventional manner and the resulting preparations can be administered, orally or parenterally, to mammals including man. The dosage to be administered depends to a large extent on the particular compound or its combination with other specific compounds being used, the particular composition formulated, the route of administration, the nature and condition of the patient and the particular situs and organ being treated. The dosage should be optimized according to the disease to be treated, the condition of the patient and other factors but generally the usual oral dosage for adult humans is 0.1 mg to 500 mg/day and preferably 5 mg to 200 mg/day. It is also observed that the combined use of two or more compounds of formula (I) exhibits a more potent nerve growth factor secretion inducing activity than that expected from the use of one of the compounds of formula (I) alone.

The nerve growth factor secretion inducing composition of the invention is useful for the treatment and prophylaxis of functional disorders of the brain in mammalian animals including human, and anticipated indications include familial dysautonomia, neurofibroma, neuroblastoma, melanocytoma, senile dementia, Alzheimer's disease and so on.

The nerve growth factor secretion inducing compounds of formula (I) of the invention have potent NGF secretion inducing activity with low toxicity and high safety.

The invention will be explained more concretely by the following test and preparation examples, but they should not be interpreted as limiting the invention in any manner.

TEST EXAMPLE i) Experimental materials and method

The study of NGF biosynthesis using astroglial cells is a very interesting line of research in connection with senile dementia of the Alzheimer's disease type. Therefore, the NGF biosynthesis promoting activity of the compound (I) of the invention was studied using mouse astroglial cells (MB-8 cells). In the study, MB-8 cells in the stationary phase were used since these were considered to be closer to the condition in the normal brain than the cells in the growth phase.

a) Experimental materials

DMEM (Dulbecco's modified Eagle medium) was purchased from Nissui Pharmaceutical Co., Ltd (Japan), fetal calf serum (FCS) from Bocknek, and streptomycin sulfate and benzylpenicillin potassium from Meiji Seika Kaisha, Ltd (Japan). The 24-well microtiter plate manufactured by Falcon was used. All the other reagents were of commercial special reagent grade.

b) Method

Culture of MB-8 cells

The astroglial (MB-8) cells from the brain of 8-day-old mice were cultured in DMEM containing 10% FCS, glutamine (2 mM), penicillin (100 units/ml) and streptomycin (100 μg/ml) in a carbon dioxide gas incubator (37° C., 5% $CO_2$). The procedure was repeated several times until confluent growth was obtained. Then, the cells were further cultured in DMEM containing 5% BSA in lieu of FCS for about 10 days to bring the cells into a stationary phase of growth. The resulting cells were grown for 24 hours in DMEM containing 0.5% BSA to which various compounds had been added. The supernatant was collected and the NGF content was determined by the enzyme immunoassay method using mouse β NGF as mentioned hereinbelow.

ii) Enzyme immunoassay (EIA) of NGF

Anti-mouse β-NGF antibody immunoglobulin G (IgG) (10 μl, 10 μg/ml) which was prepared through Protein A-Sepharose CL-4B and diluted with 0.05M Tris-HCl buffer (pH 8.3), was distributed into the wells of a polystyrene microtiter plate (Falcon 3910; 96-well) and allowed to stand at room temperature for 2 hours to adsorb the anti-mouse β NGF antibody IgG. After recovery of the antibody solution, the plate was washed three times with 100μl aliquots of a washing buffer (0.1M Tris-HCl buffer containing 0.4M sodium chloride, 0.1% BSA, 0.1% sodium azide and 1 mM magnesium chloride; pH 7.6). Then, 150 μl of the washing buffer was added and the plate was allowed to block for 1 hr. After the washing buffer was aspirated off, 25 μl aliquots of either the sample or the standard NGF solution (as diluted with the same buffer as for the sample) were added to the wells and the plate was allowed to stand at room temperature for 4 hours. The plate was then washed three times with 100 μl aliquots of the washing buffer and 30 ml aliquots of a biotinylated anti-β NGF antibody solution diluted with the washing buffer (35 ng/ml) were added. The plate was allowed to stand at 4° C. overnight. After washing, 30 μl of β-D-galactosidase-labeled streptavidin (diluted 200-fold) was added and the plate was allowed to stand at room temperature for 1 hour. The activity of the β-D-galactosidase immobilized on the solid phase was estimated by measuring the fluorescene of the 4-methylumbeliferone produced by enzyme reaction with the substrate, 4-methylumbelliferyl-β-galactoside. Thus, after the plate was washed 3 times, 30 μl aliquots of the substrate (10 μg/ml) were added and the reaction was conducted at room temperature for 3 hours. The enzymatic reaction was stopped by adding 150 μl of 0.1M glycine-sodium hydroxide buffer (pH 10.3) and the reaction systems were transferred to test tubes each containing 2.0 ml of the reaction stopper. The intensity of fluorescence in each tube was measured at an excitation wavelength of 360 nm and an emission wavelength of 450 nm. The fluorophotometer was calibrated by adjusting the fluorescence intensity of 0.1N sulfuric acid containing 1 μg/ml of quinine to 100.

iii) Results a) The standard curve of mouse β NGF

The EIA standard curve of mouse β NGF according to the established B-SA system method is shown in FIG. 1. While determinations were performed over the range of 0.15 pg/ml to 9 ng/ml, the curve flattened into a plateau after 9 pg/ml. The measuring range was 1 pg/ml to 9 ng/ml.

The background was low and the differential in the intensity of fluorescence between 1 pg/ml and 9 ng/ml was about 100-fold so that it was easy to read the concentration of NGF. The sensitivity of this assay method was as high as about 1 pg/ml.

b) The effect of the compound of the invention on the synthesis and secretion of NGF in MB-8 cells.

Figure 2:
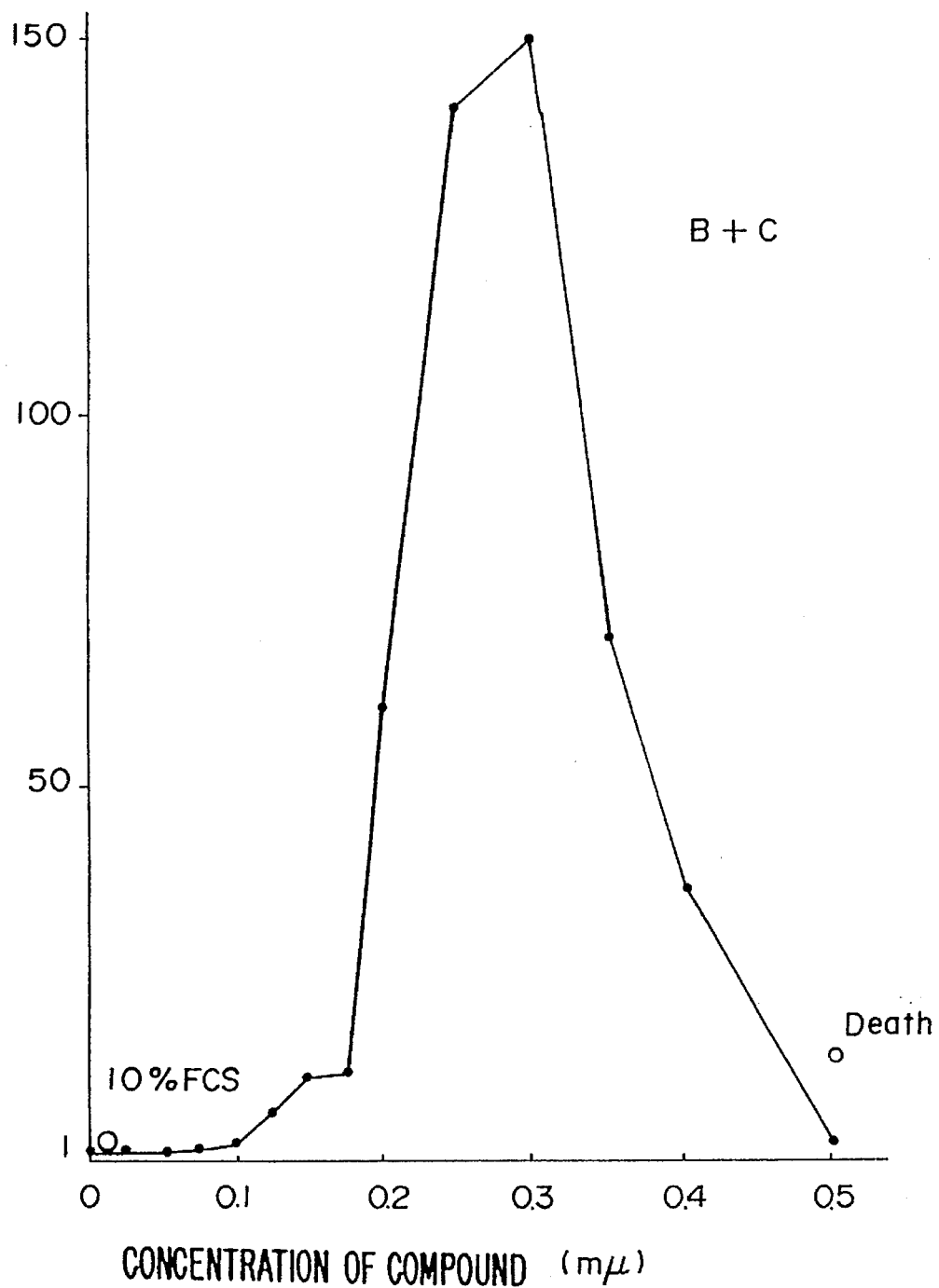
FIG. 2 shows the NGF secretion inducing effects of the first recrystallized mixture of Compounds (B) and (C).
Figure 3:
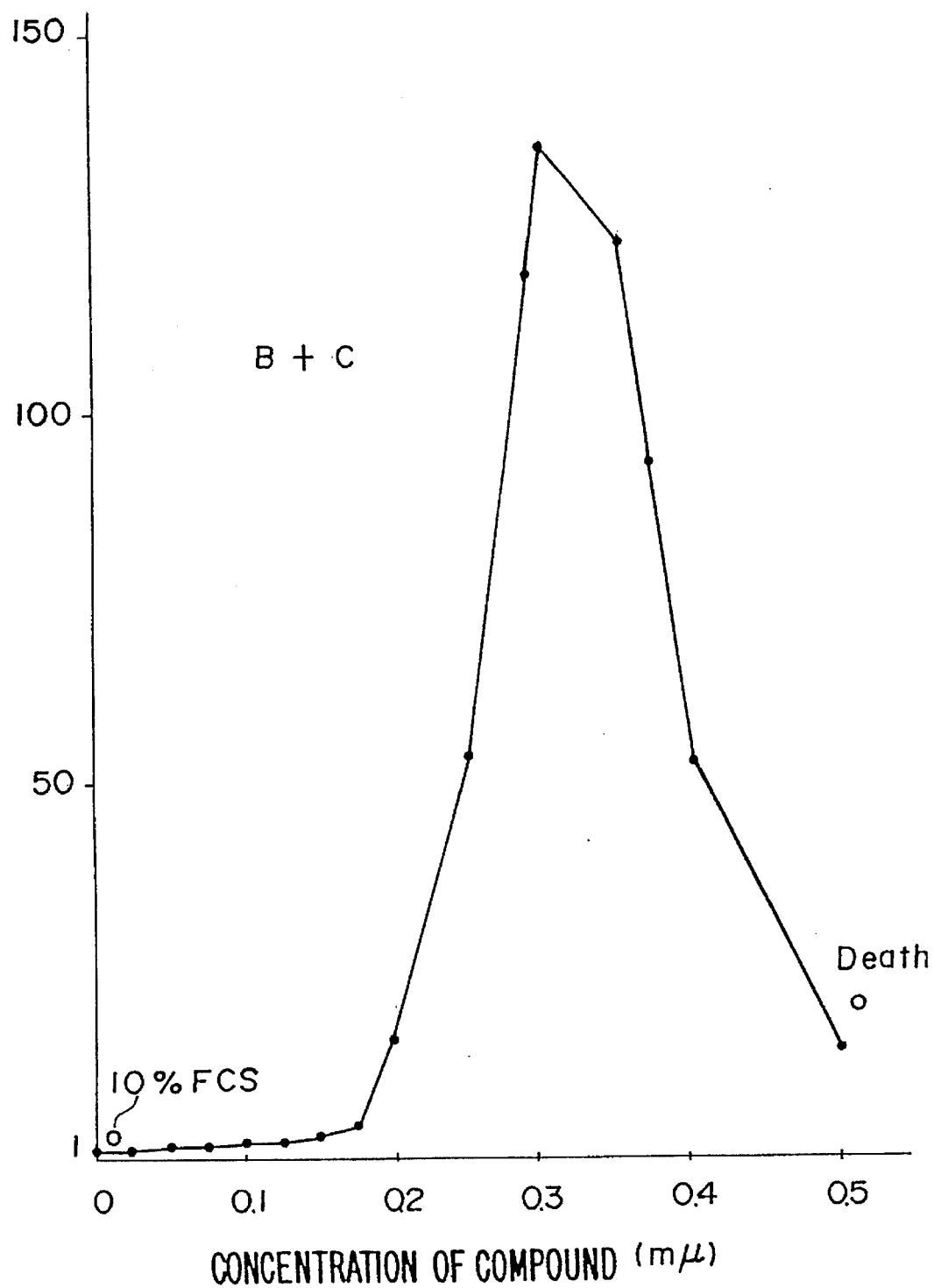
FIG. 3 shows the NGF secretion inducing effects of the mixture of Compounds (B) and (C) (composition ratio; (B) 0.25 g+(C) 0.81 g).
Figure 4:
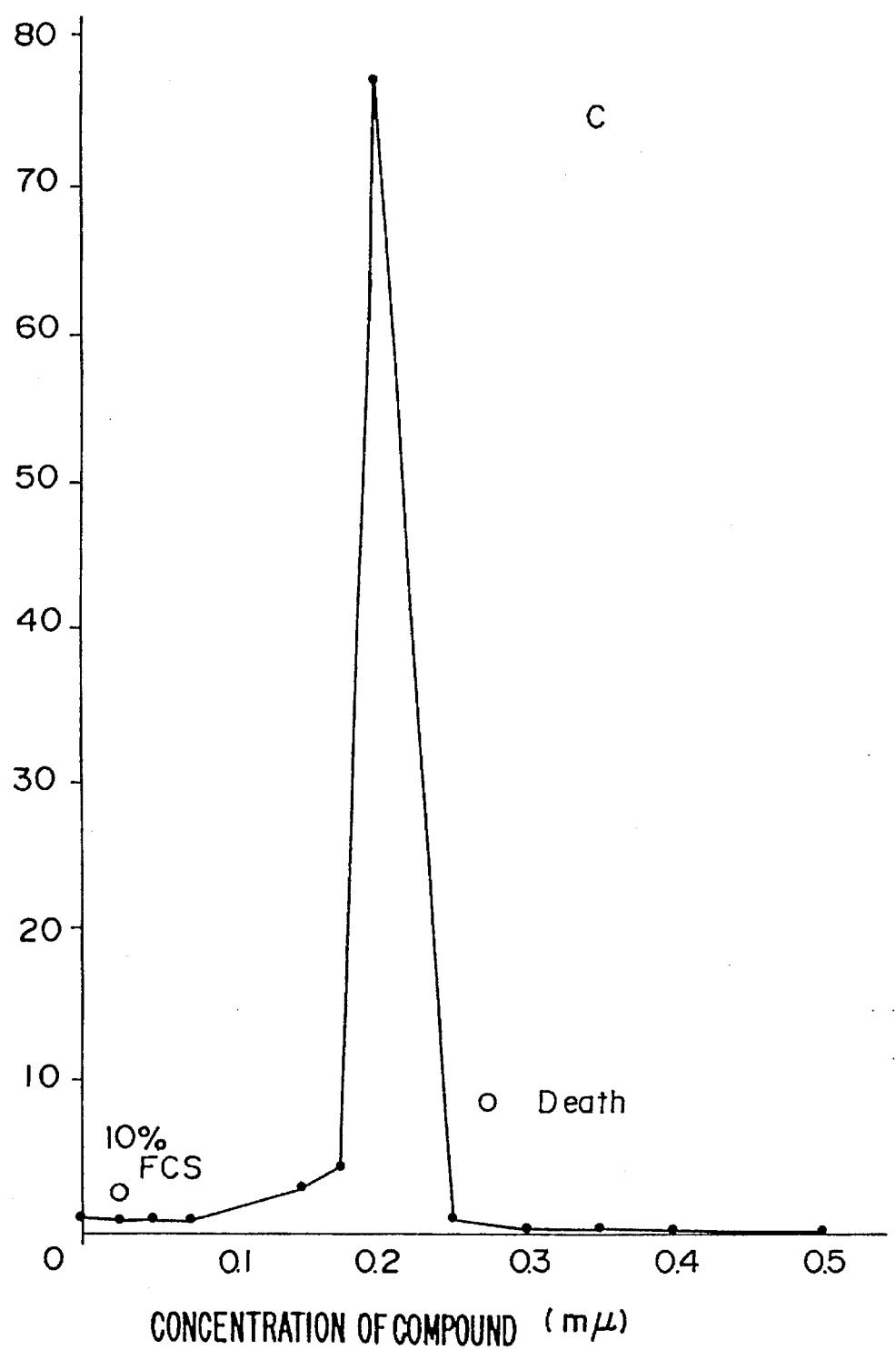
FIG. 4 shows the NGF secretion inducing effects of (C).

The NGF secretion inducing effects of the compound (I) of the present invention are shown in FIGS. 2 to 4.

FIG. 2 shows the NGF secretion inducing effects of the first recrystallized mixture of Compound (B) and Compound (C) (composition ratio; not determined).

FIG. 3 shows the NGF secretion inducing effects of the mixture of Compound (B) and Compound (C) (second recrystallized product, composition ratio; (B) 0.25 g+ (C) 0.81 g).

FIG. 4 shows the NGF secretion inducing effects of Compound (C).

WORKING EXAMPLE 1 (PREPARATION EXAMPLE)

To a mixed solution of pyridine (10 ml) and aniline (2 ml) were added 2,5-dihydroxybenzaldehyde (1.1 g, 1 mM) and malonic acid (1.6 g, 1.5 mM) and the reaction mixture was stirred at 70° C. for 10 hours and concentrated in vacuo to a half volume. The concentrate was poured into an aqueous 2N HCl solution (50 ml) and extracted with ethyl acetate (40 ml). The extract was dried over anhydrous sodium sulfate (5 g) and concentrated to dryness. The residue was purified by column chromatography on silica gel (200 g of silica, column size: 30 mm (diameter)×900 mm(height)). The column was eluted with benzene-acetone (2:1, v/v, 31) to give first Compound A (45 mg), next Compound B (150 mg) and finally Compound C (1.03 mg).

A. (6-Hydroxy-2-oxo-2H-chromene-3-carboanilide):

Recrystallization from ethanol gave yellow needles.

m.p.: 284°–286° C. (decomp.) EIMS (electron impact mass spectrum, m/z, %): 281 ($M^+$,40), 189 (100), 161 (4), 105 (21). Elemental analysis for $C_{16}H_{11}O_4N$: Calculated: C, 68.32; H, 3.94; N, 4.98. Found: C, 68.17; H, 3.97; N, 4.95. IR ($v^{KBr}cm^{-1}$): 3300. 1710, 1695, 1595, 1570, 1555, 1500, and 1440. UV ($\lambda^{MeOH}$nm (log ε)): 207 (4.42), 229 (4.36), 304 (4.22), and 370 sh ( 3.90 ).

$^1$HNMR (acetone-$d_6$, 270 MHz, δ): 7.15 (1H, br t, J=7 Hz, H-4'), 7.20 (1H, dd, J=8.2 Hz, H-7), 7.31 (1H, d, J=2 Hz, H-5), 7.38 (2H, t, J=7 Hz, H-3', 5'), 7.41 (1H, d, J=8 Hz, H-8), 7.73 (2H, br d, J=7 Hz, H-2', 6'), 8.86 (1H, s, OH), 10.73 (1H, br s, NH), 10.75 (1H, br s, H-4).

$^{13}$C-NMR (acetone-$d_6$, 67.5 MHz, δ): 160.7 (s, C-2), 119.6 (s, C-3), 147.5 (d, C-4), 113.8 (d, C-5), 154.4 (s, C-6), 122.6 (d, C-7), 117.2 (d, C-8), 147.3 (s, C-8a), 119.7 (s, C-4a), 159.9 (s, CONH), 138.8 (s, C-1'), 119.8 (d, C-2', 6'), 129.0 (d, C-3', 5'), 124.3 (d, C-4').

B. (6-Hydroxy-3,4-dihydro-2-oxo-2H-chromen-4-ylacetoanilide):

Recrystallization from ethanol gave colorless plates.

m.p.: 218°–219° C. EIMS (m/z, %): 297 ($M^+$, 30), 238 (4), 176 (7), 163 (38), 135 (85), 107 (17), and 93 (100). Elemental analysis for $C_{17}H_{15}O_4N$: Calculated: C, 68.67; H, 5.08; N, 4.71. Found: C, 68.58; H, 5.15; N, 4.70. IR ($v^{KBr}cm^{-1}$): 3350, 1715, 1665, 1602, 1540, 1503, 1485, 1190. UV ($\lambda^{MeOH}$nm (log ε)): 206 (4.52), 240 (4.43), 285 (3.54).

$^1$HNMR (acetone-$d_6$, 270 MHz, δ): 2.58 (2H, m, H-3), 2.67 (1H, dd, J=17.5 Hz, H-9), 2.97 (1H, dd, J=17.5 Hz, H-90), 3.51 (1H, m, H-4), 6.65 (1H, dd, J=8, 2 Hz, H-7), 6.69 (1H, d, J=2 Hz, H-5), 6.90 (1H, d, J=8 Hz, H-8), 7.00 (1H, t, J=7 Hz, H-4'), 7.31 (2H, t, J=7 Hz, H-3', 5'), 7.55 (2H, br d, J=7 Hz, H-2', 6'), 9.40 (1H, s, OH), 9.95 (1H, br s, NH).

$^{13}$C-NMR (acetone-$d_6$, 67.5 MHz, δ): 168.5 (s, C-2), 41.2 (t, C-3), 31.3 (d, C-4), 113.8 (d, C-5), 153.8 (s, C-6), 114.7 (d, C-7), 117.8 (d, C-8), 131.3 (s, C-4a), 143.6 (s, C-8a), 33.9 (t, C-9), 168.1 (s, C-10), 139.6 (s, C-1'), 119.6 (d, C-2', 6'), 128.9 (d, C-3', 5'), 123.4 (d, C-4').

C. (β-(2,5-Dihydroxyphenyl)glutaric acid dianilide):

Recrystallization from acetone gave colorless needles.

m.p.: 177°–178° C. (acetone- n-hexane) EIMS (m/z, %): 390 ($M^+$, —), 297 (30), 238 (4), 176 (8), 163 (38), 135 (86), 107 (17), and 93 (100). Cation FABMS (m/z): 391.1685 ($M^+$-H), Calculated ($C_{23}H_{22}O_4N_2$), 391.1658. Elemental analysis for $C_{23}H_{22}O_4N_2$: Calculated: C, 70.75; H, 5.68; N, 7.18. Found: C, 71.18; H, 5.71; N, 7.11. IR ($v^{KBr}cm^{-1}$): 3330, 1675, 1650, 1595, 1540, 1500, and 1445. UV (λ

$^{MeOH}$nm (log ε)): 205 (4.62), 242 (4.51), and 297 (3.68).
$^1$HNMR (acetone-d$_6$, 270 MHz, δ): 3.72 (4H, m, H-8, 10), 3.87 (1H, m, H-7), 6.38 (1H, dd, J=8, 2 Hz, H-4), 6.5 (1H, d, J=8 Hz, H-3), 6.59 (1H, d, J=2 Hz, H-6), 6.98 (2H, t, J=7 Hz,H-4',4"), 7.23 (4H, t, J=7 Hz, H-3', 5' and 3", 5"), 7.53 (4H, br d, J=7 Hz, H-2', 6' and 2", 6"), 8.54, 8.67 (1H, each s, OH), 9.84 (2H, br s, NH×2).
$^{13}$C-NMR (acetone-d$_6$, 67.5 MHz, δ): 130.4 (s, C-1), 147.2 (s, C-2), 115.8 (d, C-3), 113.2 (d, C-4), 149.6 (s, C-5), 115.2 (d, C-6), 33.0 (d, C-7), 40.6 (t, C-8, 10), 170.0 (s, C-9, 11), 139.2 (s, C-1', 1"), 119.1 (d, C-2', 6', C-2", 6"), 128.6 (d, C-3', 5', C-3", 5"), 122.9 (d, C-4', 4").

WORKING EXAMPLE 2 (PREPARATION EXAMPLE)

To a mixed solution of pyridine (40 ml) and aniline (15 ml) were added 2,5-dihydroxybenzaldehyde (4.2 g, 35 mM) and malonic acid (12 g, 0.1M) and the reaction mixture was stirred at 90° C. for 10 hours and treated in the same manner as in Working Example 1 to afford Compound A (110 mg), Compound B (380 mg) and Compound C (4.7 mg).

WORKING EXAMPLE 3 (PREPARATION EXAMPLE)

Into a solution of pyridine (2 ml) in a 50 ml round flask were dissolved 2,5-dihydroxybenzaldehyde (212 mg, 2 mM) and malonic acid (312 mg, 3 mM) followed by addition of aniline (1 ml) and the reaction mixture was treated under the conditions (3-1 to 3-5) mentioned below in Table 1.

After the reaction, the mixture was poured into a 1N HCl solution (30 ml), extracted, washed with water and concentrated to dryness. The production ratio ((A): (B): (C)) was measured by HPLC.

TABLE 1

| | Reaction Temperature (°C.) | Reaction Time (h) | Ratio (A): | (B): | (C) |
|---|---|---|---|---|---|
| 3-1 | 125 | 10 | 9.8 | 6.9 | 19.5 |
| 3-2 | 90 | 10 | 4.6 | 5.7 | 22.5 |
| 3-3 | 70 | 10 | 14.0 | 16.1 | 53.1 |
| 3-4 | 70 | 20 | 3.1 | 5.9 | 27.5 |
| 3-5 | 60 | 10 | 6.7 | 10.4 | 46.5 |

FORMULATION EXAMPLE 1

| (1) Compound B | 5 g |
|---|---|
| Compound C | 16 g |
| (2) Lactose | 198 g |
| (3) Corn starch | 40 g |
| (4) Magnesium stearate | 2 g |

The above ingredients (1) and (2) and a paste prepared from a 15 g portion of corn starch (3) were mixed and granulated, followed by adding a 10 g portion of corn starch and (4). The resulting mixture was compression-molded to prepare 1000 tablets measuring 5 mm in diameter and each containing 20 mg of (1).

What is claimed is:
1. A compound of the formula

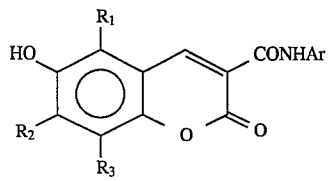

wherein $R_1$, $R_2$ and $R_3$ are independently hydrogen, a lower alkyl or lower alkoxy group and Ar is an aromatic group of 6–10 carbon atoms which is unsubstituted or is substituted by halogen, hydroxy, lower alkyl, lower alkoxy or nitro or a pharmaceutically acceptable salt thereof.

2. A compound of the formula

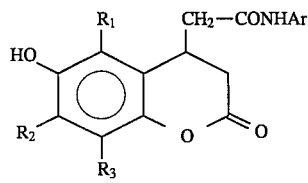

wherein $R_1$, $R_2$ and $R_3$ are independently hydrogen, a lower alkyl or lower alkoxy group and Ar is an aromatic group of 6–10 carbon atoms which is unsubstituted or is substituted by halogen, hydroxy, lower alkyl, lower alkoxy or nitro or a pharmaceutically acceptable salt thereof.

3. A compound according to claim 1, which is a compound of the formula

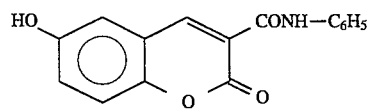

or a pharmaceutically acceptable salt thereof.

4. A compound according to claim 2, which is a compound of the formula:

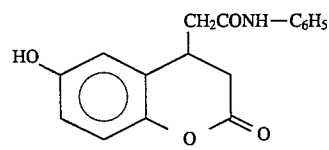

or a pharmaceutically acceptable salt thereof.

5. A pharmaceutical composition exerting nerve growth factor secretion inducing activity which comprises an effective amount of at least one compound selected from compounds of the formulae

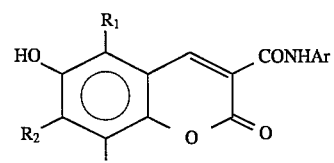

and

-continued

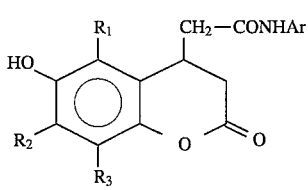

wherein $R_1$, $R_2$ and $R_3$ are independently hydrogen, a lower alkyl or lower alkoxy group and Ar is an aromatic group of 6–10 carbon atoms which is unsubstituted or is substituted by halogen, hydroxy, lower alkyl, lower alkoxy or nitro or a pharmaceutically acceptable salt thereof in admixture with a pharmaceutically acceptable carrier or diluent.

6. A pharmaceutical composition according to claim 5 containing a compound of the formula

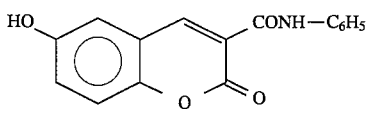

or a pharmaceutically acceptable salt thereof.

7. A pharmaceutical composition according to claim 5 containing a compound of the formula

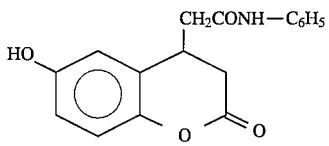

or a pharmaceutically acceptable salt thereof.

8. A pharmaceutical composition according to claim 5 containing a mixture of a compound of the formula

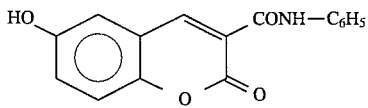

or a pharmaceutically acceptable salt thereof and a compound of the formula

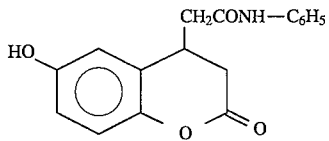

or a pharmaceutically acceptable salt thereof.

9. A method for the treatment of a degenerative nervous system disorder which comprises administering to a mammal in need of such treatment an effective amount of at least one compound selected from compounds of the formulae

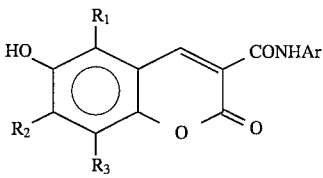

and

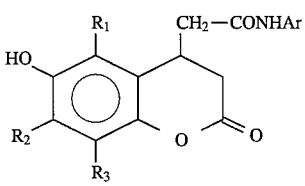

wherein $R_1$, $R_2$ and $R_3$ are independently hydrogen, a lower alkyl or lower alkoxy group and Ar is an aromatic group of 6–10 carbon atoms which is unsubstituted or is substituted by halogen, hydroxy, lower alkyl, lower alkoxy or nitro or a pharmaceutically acceptable salt thereof.

10. A method for inducing nerve growth factor secretion which comprises administering to a mammal in need of such induction an effective amount of at least one compound selected from compounds of the formula

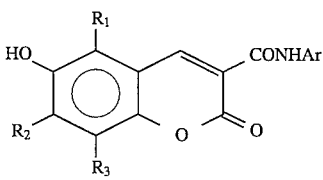

and

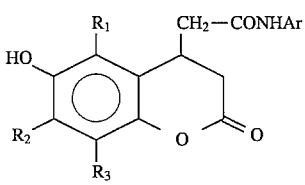

wherein $R_1$, $R_2$ and $R_3$ are independently hydrogen, a lower alkyl, or lower alkoxy group and Ar is an aromatic group of 6–10 carbon atoms which is unsubstituted or is substituted by halogen, hydroxy, lower alkyl, lower alkoxy or nitro or a pharmaceutically acceptable salt thereof.

\* \* \* \* \*